United States Patent [19]

Lansbarkis et al.

[11] Patent Number: 5,449,853
[45] Date of Patent: Sep. 12, 1995

[54] PROCESS FOR SEPARATING HYDROCARBONS USING ALKYLENE-BRIDGED POLYSILSESQUIOXANES

[75] Inventors: James R. Lansbarkis, El Dorado, Calif.; Timothy A. Brandvold, Buffalo Grove, Ill.

[73] Assignee: UOP, Des Plaines, Ill.

[21] Appl. No.: 356,613

[22] Filed: Dec. 16, 1994

[51] Int. Cl.$^6$ .............................................. C07C 7/12
[52] U.S. Cl. .................................. 585/825; 585/826; 585/830
[58] Field of Search .................. 585/825, 826, 830

[56] References Cited

U.S. PATENT DOCUMENTS

| | | | |
|---|---|---|---|
| 2,985,589 | 5/1961 | Broughton et al. | 210/34 |
| 4,036,744 | 7/1977 | Rosback et al. | 208/310 |
| 4,048,111 | 9/1977 | Rosback et al. | 252/455 Z |

OTHER PUBLICATIONS

Shea, K. J., Loy, D. A., *Chemistry of Materials*, 1989, 1, pp. 572–574.
Shea, K. J., Loy, D. A., Webster, O., *J. Am. Chem. Soc.*, 1992, pp. 6700–6710.
Shea, K. J., Loy, D. A., Webster, O., *Mater. Res. Soc. Symp. Proc.*, 1990, 180, pp. 975–980.
Shea, K. J., Loy, D. A., Webster, O., *Polym. Mater. Sci. Eng.*, 1990, 63, pp. 281–285.
Oviatt, H. W., Shea, K. J., Small, J. H., *Chem. Mater.*, 1993, 5, pp. 943–950.
Small, J. H., Shea, K. J., Loy, D. A., *J. Non-Crystalline Solids*, 1993, 160, pp. 234–246.

*Primary Examiner*—Asok Pal
*Assistant Examiner*—Nhat D. Phan
*Attorney, Agent, or Firm*—Thomas K. McBride; Eugene I. Snyder

[57] ABSTRACT

A process to separate at least two classes of hydrocarbons of a solution using an alkylene-bridged polysilsesquioxane adsorbent has been developed. The classes of hydrocarbons to be separated may be saturated hydrocarbons, unsaturated aliphatic hydrocarbons and aromatic hydrocarbons. The alkylene-bridging group may contain from about 2 to about 14 carbon atoms. A specific embodiment of the invention is one where the components of a solution of aromatic, unsaturated aliphatic, and saturated hydrocarbons are separated into an aromatic hydrocarbon portion, an unsaturated aliphatic hydrocarbon portion, and a saturated hydrocarbon portion where the adsorbent is an alkylene-bridged polysilsesquioxane.

23 Claims, 4 Drawing Sheets

PROCESS FOR SEPARATING HYDROCARBONS USING ALKYLENE-BRIDGED POLYSILSESQUIOXANES

BACKGROUND OF THE INVENTION

Processes to separate hydrocarbon mixtures into component portions are an important necessity in industry and can employ a wide variety of techniques. Some separation processes involve contacting the hydrocarbon mixture with a membrane through which one component type is able to permeate. For example, U.S. Pat. No. 5,039,422 disclosed using a urea polymer chain extender with a compatible second prepolymer membrane to separate aromatic hydrocarbons from a mixture of aromatic and non-aromatic hydrocarbons. Other separation processes involve solvent extraction such as using tetrahydrothiophene 1,1-dioxide to recover high purity aromatic hydrocarbons such as benzene, toluene, and xylenes from hydrocarbon mixtures, see Wheeler, T. In *Handbook of Petroleum Refining Processes;* Meyers, R. A., Ed.; McGraw-Hill Book Company: New York, 1986, Chapter 8.4. A third type of separation process includes using a solid adsorbent to selectively adsorb desired components from the mixture. The components are later desorbed and recovered; see U.S. Pat. No. 4,048,111.

The separation of mixtures of hydrocarbons according to whether components are aliphatic or aromatic, and separations of the aliphatic hydrocarbons according to whether components are saturated or unsaturated are examples of separation processes that may be carried out using a solid adsorbent. The term aliphatic means those compounds which are not aromatic. Typically the solid adsorbents used in industry are zeolites or molecular sieve materials such as those described in U.S. Pat. Nos. 4,036,744 and 4,048,111. The present invention expands the range of useful solid adsorbents to effect hydrocarbon separations to include alkylene-bridged polysilsesquioxanes. Specific organically-bridged polysilsesquioxane materials and their preparation have been disclosed in Shea, K. J., Loy, D. A. *Chem. Mater.* 1989, 1, pp. 572–574; Shea, K. J., Loy, D. A., Webster, O. *J. Am. Chem. Soc.* 1992, 114, pp. 6700–6710; Shea, K. J., Loy, D. A., Webster, O. *Mater. Res. Soc. Symp. Proc.* 1990, 180, pp. 975–980; Shea, K. J., Loy, D. A., Webster, O. *Polym. Mater. Sci. Eng.* 1990, 63, pp. 281–285. Specific alkylene-bridged polysilsesquioxanes and their preparation have been disclosed in Oviatt, H. W., Shea, K. J., Small, J. H. *Chem. Mater.* 1993, 5, pp. 943–950 and Small, J. H., Shea, K. J., Loy, D. A. *J. Non-Crystalline Solids* 1993, 160, pp. 234–246. This art teaches that organic groups can be introduced at regular intervals in an inorganic silicate framework, thus forming a three-dimensional organic-inorganic hybrid silicate-like polymeric material, also called an organically-bridged polysilsesquioxane. A two-dimensional representation of the well-known inorganic silicate framework is shown in I, and an analogous representation of the organically-bridged polysilsesquioxane where the represents the organic bridging group is shown in II. Of course, frameworks I and II, in reality, extend to form a three-dimensional, continuous, amorphous solid.

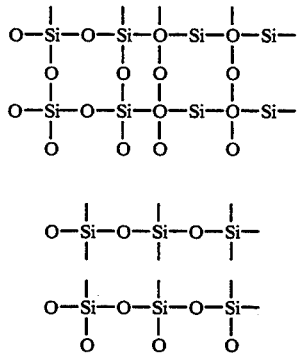

The specific alkylene-bridging groups disclosed in the art include ethylene, tetramethylene, hexamethylene, octamethylene, decamethylene, and tetradecamethylene. In view of the prior art, alkylene-bridging groups of trimethylene, pentamethylene, heptamethylene, nonamethylene, undecamethylene, dodecamethylene, tridecamethylene and their preparation are readily apparent to those skilled in the art. Organically-bridged polysilsesquioxanes containing these bridging groups are termed alkylene-bridged polysilsesquioxanes. One stated objective of the disclosed work was to provide molecular level control of the morphology of the framework, another was to provide a new chromatographic support, and a third was use in optical applications. However, applicant has found that these materials perform as adsorbents for saturated, unsaturated aliphatic, and aromatic hydrocarbons at low temperatures. Furthermore, applicant has discovered that adsorbed saturated, unsaturated aliphatic, and aromatic hydrocarbons may be desorbed from the alkylene-bridged polysilsesquioxanes using environmentally preferred saturated hydrocarbon desorbents.

SUMMARY OF THE INVENTION

The purpose of the invention is to provide an adsorptive process to separate at least two classes of hydrocarbons selected from the group consisting of aromatic, unsaturated aliphatic, and saturated hydrocarbons where the adsorbent to effect the separation is an alkylene-bridged polysilsesquioxane where the alkylene-bridging group contains from about 2 to about 14 carbon atoms. A specific embodiment is one where the components of a solution of aromatic, unsaturated aliphatic, and saturated hydrocarbons are separated into an aromatic hydrocarbon portion, an unsaturated aliphatic hydrocarbon portion, and a saturated hydrocarbon portion where the adsorbent is an alkylene-bridged polysilsesquioxane. Another specific embodiment is one where the adsorptive process is used to separate aromatic hydrocarbons from a solution of aromatic and aliphatic hydrocarbons. Yet another specific embodiment is one where unsaturated aliphatic hydrocarbons are separated from a solution of unsaturated aliphatic and saturated hydrocarbons.

DETAILED DESCRIPTION OF THE INVENTION

Figure 1:
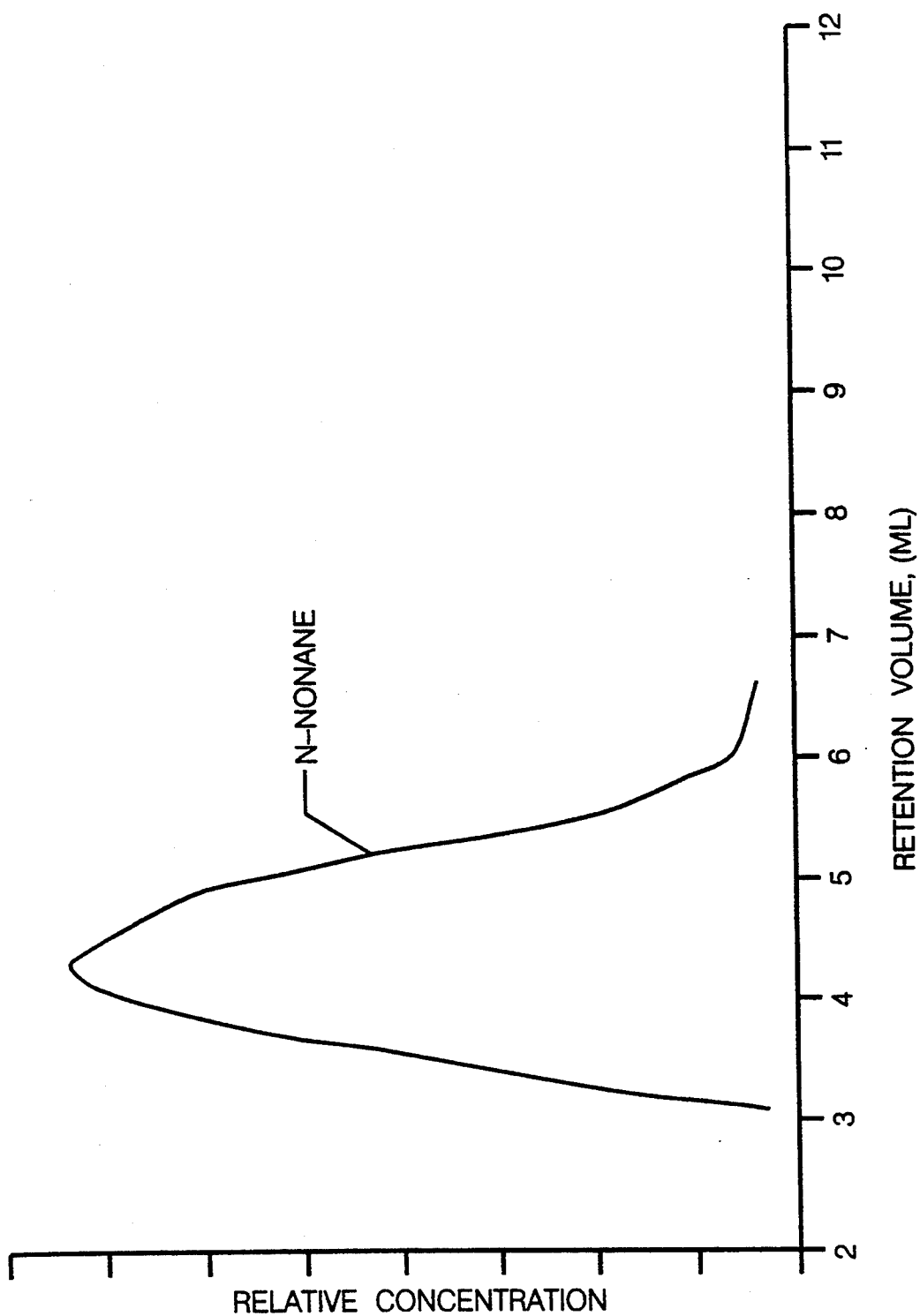
FIG. 1 is the chromatographic plot of the separation of aromatic hydrocarbons from a mixture of a saturated hydrocarbon and aromatic hydrocarbons using silica gel as the adsorbent as conducted in Example 1.

The subject inventive process is that of separating, into hydrocarbon classes, the components of a solution containing at least two classes of hydrocarbons where the classes may be saturated hydrocarbons, unsaturated aliphatic hydrocarbons, and aromatic hydrocarbons. Example separations include (1) separating the components of a solution of saturated hydrocarbons and unsaturated aliphatic hydrocarbons into a saturated hydrocarbon portion and an unsaturated aliphatic hydrocarbon portion; (2) separating the components of a solution of saturated hydrocarbons and aromatic hydrocarbons into a saturated hydrocarbon portion and an aromatic hydrocarbon portion; (3) separating the components of a solution of unsaturated aliphatic hydrocarbons and aromatic hydrocarbons into an unsaturated aliphatic hydrocarbon portion and an aromatic hydrocarbon portion; (4) separating the components of a solution of saturated hydrocarbons, unsaturated aliphatic hydrocarbons, and aromatic hydrocarbons into a saturated hydrocarbon portion, an unsaturated aliphatic hydrocarbon portion, and an aromatic hydrocarbon portion; and (5) separating the components of a solution of saturated hydrocarbons, unsaturated aliphatic hydrocarbons, and aromatic hydrocarbons into a saturated and unsaturated aliphatic hydrocarbon portion and an aromatic hydrocarbon portion.

The separations are accomplished by utilizing the surprising adsorptive properties of alkylene-bridged polysilsesquioxanes, specifically where the alkylene-bridging group contains from about 2 to about 14 carbon atoms. Unexpectedly, the alkylene-bridged polysilsesquioxane adsorbents perform best when the process is operated at low temperatures, typically from about 30° to about 80° C., as compared to the zeolitic and molecular sieve adsorbents currently used in industry which perform optimally at about 100° to about 200° C. Lower operating temperatures provide advantages such as reduced utility costs and decreased undesired reactivity among the components of the solution to be separated. Furthermore, the adsorptive and desorptive capabilities of the alkylene-bridged polysilsesquioxanes are unexpected since silica gel, which has a structure somewhat analogous to the alkylene-bridged polysilsesquioxane, when used under similar conditions permanently retained the aromatic hydrocarbon portion of a mixture of a saturated hydrocarbon and aromatic hydrocarbons; see Example 1.

An additional surprising feature of the alkylene-bridged polysilsesquioxane is the capacity for near simultaneous desorption of all components within a hydrocarbon class. Generally, in adsorption-desorption processes, compounds within a hydrocarbon class desorb in a gradient from the least strongly adsorbed to the most strongly adsorbed, usually due to characteristics such as the degree of branching. Attempts to consolidate all desorption of a hydrocarbon class and thereby achieve simultaneous desorption of the class instead frequently drove the least strongly adsorbed compound to desorb so quickly that it became intermixed with the previous eluting hydrocarbon class or the non-retained components. The desorption of adsorbed components in the current invention also proceeds in a gradient, but operating conditions may be controlled so that the gradient within a hydrocarbon class is negligible and effectively all components of the hydrocarbon class desorb simultaneously but yet separate from other hydrocarbon classes. The system is flexible, however, when only one class of hydrocarbons is present, the operating conditions may be optimized to increase the gradient within that hydrocarbon class in order to be able to separate components within a class.

A specific embodiment of the invention is the separation of a solution of aromatic, unsaturated aliphatic, and saturated hydrocarbons into an aromatic hydrocarbon portion, an unsaturated aliphatic hydrocarbon portion, and a saturated hydrocarbon portion. In general terms, the solution would be contacted with the alkylene-bridged polysilsesquioxane adsorbent which would adsorb the hydrocarbons with increasing strength in the order of saturated hydrocarbons < unsaturated aliphatic hydrocarbons < aromatic hydrocarbons. The desorbent would be added to the system, and the weakly adsorbed saturated hydrocarbons would be desorbed first, removed from the system, and collected. The unsaturated aliphatic components would be desorbed by the desorbent next since they are less strongly retained by the adsorbent as compared to the aromatic hydrocarbons. Once desorbed, the unsaturated aliphatic components would be removed from the system and collected. The aromatic components would be desorbed last since they are the most strongly retained by the adsorbent. The desorbed aromatic components would also be removed from the system and collected. The collected hydrocarbons would then be recovered using a conventional technique such as fractional distillation.

The alkylene-bridged polysilsesquioxane adsorbent may be used in any of the commonly known solid adsorbent systems such as fixed bed, moving bed, and simulated moving bed. In a fixed bed system, increments of the solution to be separated and desorbent are contacted alternately with the adsorbent which is stationary. As the solution components move through the bed, they gradually separate into bands. The bands travel at different rates corresponding to how strongly the components are retained by the adsorbent. As the separated bands elute from the bed, they are collected. Since different bands elute sequentially, the process is semi-continuous. The size of the fixed bed system may vary from a commercial scale system to an analytical scale system, depending upon the application. In a moving bed process, the adsorbent is physically conveyed through the system counter to the continuously introduced fluid streams. While it is possible to use the alkylene-bridged polysilsesquioxane adsorbent in a moving bed system, it is the least preferred due to typical problems caused by the physical movement of the solid such as attrition and maintaining a uniform flow. Additional information regarding fixed bed and moving bed systems may be found in Mowry, J. R. In *Handbook of Petroleum Refining Processes;* Meyers, R. A., Ed.;

McGraw-Hill Book Company: New York, 1986, Chapter 8.8.

The most preferred system for alkylene-bridged polysilsesquioxane adsorbents is the simulated moving bed system. As with the moving bed, in the simulated moving bed system, the solution to be separated and the desorbent are continuously fed to the system and adsorption and desorption are continuously taking place. In this broad embodiment, the adsorption and desorption produce three product streams, an extract, an intermediate raffinate, and a raffinate stream. Simulated moving bed systems which provide for the removal of three separated product streams are somewhat unusual, the more typical case is where a solution is separated into two portions. In this embodiment, the weakly adsorbed portion of the solution, the saturated hydrocarbon portion, travels with the fluid flow of the system, is removed in the raffinate stream, and collected. The strongly adsorbed portion of the solution, the unsaturated aliphatic hydrocarbon portion, is carried with the simulated movement of the adsorbent, but is desorbed from the adsorbent with a low concentration of desorbent. At this point, the unsaturated aliphatic hydrocarbon portion is withdrawn from the system in the intermediate raffinate stream. The most strongly adsorbed portion of the solution, the aromatic portion, is also carried with the movement or simulated movement of the adsorbent, and is desorbed with a high concentration of desorbent. The aromatic hydrocarbon portion is then removed in the extract stream and collected. The raffinate stream, intermediate raffinate stream, and extract stream, in addition to containing their respective hydrocarbon portion, also contain desorbent. At a point after the separation and collection, the hydrocarbon product may be recovered from the desorbent using conventional means such as distillation.

The adsorbent of the simulated moving bed system is usually a succession of sub-beds which can be housed in one chamber, or in many chambers, and different applications may require differing numbers of sub-beds. In the countercurrent case, the shift in the locations of the inputs and outputs in the direction of the fluid flow through the bed simulates the movement of the solid adsorbent in the opposite direction. The system may also be used where the simulated movement of the adsorbent bed is cocurrent with the direction of the fluid flow. Commercially, moving the locations of the inputs and outputs is accomplished by a fluid directing device known generally as a rotary valve which works in conjunction with distributors located between the adsorbent sub-beds. The rotary valve accomplishes moving the input and output locations through first directing the introduction or withdrawal lines to specific distributors located between the adsorbent sub-beds. After a specified time period, called the step time, the rotary valve advances one index and redirects the inputs and outputs to the distributors immediately adjacent and downstream for countercurrent flow, or upstream for cocurrent flow, of the previously used distributors. Each advancement of the rotary valve to a new valve position is generally called a valve step, and the completion of all the valve steps is called a valve cycle. The step time is uniform for each valve step in a valve cycle, and ranges generally from about 10 to about 60 minutes. A typical process contains from 4 to 24 adsorbent sub-beds, an equal number of distributors located between each adsorbent sub-bed. Further explanation of operating principles and possible variations may be found in U.S. Pat. Nos. 4,313,015, 4,402,832, 4,498,991 and 4,478,721.

For liquid phase operation, the saturated and unsaturated aliphatic hydrocarbons in the solution to be separated must be liquid at the temperatures of operation, about 30° to about 80° C., and the pressures of operation should be sufficient to maintain the liquid phase. Generally acceptable hydrocarbon compounds include those having from about 4 to about 18 carbon atoms. The preferred hydrocarbons contain from about 6 to about 17 carbon atoms, and the most preferred hydrocarbons contain from about 9 to about 15 carbon atoms. The structure of the hydrocarbons may be linear, branched, or cyclic. The aliphatic unsaturated hydrocarbons may contain single or multiple double and/or triple bonds. The aromatic hydrocarbons must also be liquid at the process operating temperatures and pressures, generally allowing for aromatic compounds containing from 6 to 18 carbon atoms. Alternatively, other hydrocarbons may be used provided they are liquid in the separation process. For example, the desorbent and other components in the mixture may act as a solvent for hydrocarbons which may not otherwise be liquid under operating conditions. Additionally, it is contemplated that the invention may be performed in the gas phase. For gas phase operation, suitable hydrocarbons must have boiling points less than the temperature of operation.

For the liquid phase application, the desorbent, a liquid capable of displacing the adsorbed components, is preferably a saturated hydrocarbon. The ability to use a saturated hydrocarbon as the desorbent is a significant advantage of the invention since saturated hydrocarbons are generally less hazardous to the environment than typical currently used desorbents such as unsaturated hydrocarbons. To be used as a desorbent, the saturated hydrocarbon must be liquid at the process operating temperatures and pressures. Typical acceptable saturated hydrocarbons are those having from about 4 to about 18 carbon atoms. The structure of the saturated hydrocarbon desorbent may be linear, branched, or cyclic. The preferred desorbents are the most different in boiling point from the involved unsaturated aliphatic and aromatic hydrocarbons. The different boiling point of the desorbent as compared to the hydrocarbons being separated provides for simplified recovery of the separated hydrocarbons from the desorbent. It is further contemplated that unsaturated aliphatic hydrocarbons and mixtures of unsaturated aliphatic hydrocarbons and saturated hydrocarbons may serve as desorbents. Acceptable unsaturated aliphatic hydrocarbons include those containing from about 4 to about 18 carbon atoms. Preferred desorbents include unsaturated aliphatic hydrocarbons containing from about 4 to about 12 carbon atoms. For the gas phase application, the desorbent may be hydrogen, nitrogen or helium.

Another specific embodiment of the invention is the separation of a solution of aromatic hydrocarbons and aliphatic hydrocarbons into an aromatic hydrocarbon portion and an aliphatic hydrocarbon portion, the aliphatic portion being a combination of saturated hydrocarbons and unsaturated aliphatic hydrocarbons; see Example 4. The requirements for acceptable aliphatic hydrocarbons and aromatic hydrocarbons discussed above also apply in this specific embodiment. The preferred operation of this embodiment is also in a countercurrent simulated moving bed mode. In this case however, since there are only two separated portions, a more common simulated moving bed system, such as that disclosed in U.S. Pat. No. 2,985,589, may be used. The primary difference of the system appropriate to this specific embodiment as compared to the system earlier discussed is the elimination of the intermediate raffinate stream. In this embodiment, the aliphatic hydrocarbons are carried with the fluid flow, removed from the system in the raffinate stream, and collected. The aromatic hydrocarbons are adsorbed by the alkylene-bridged polysilsesquioxane and are carried with its simulated movement. When the desorbent concentration is high enough, the aromatic hydrocarbons are desorbed, removed from the system in the extract stream, and collected. A specific application of this embodiment is the removal of aromatic hydrocarbons containing from about 6 to about 18 carbon atoms from linear alkylbenzene production process streams to prevent catalyst deactivation. For example, the aromatic hydrocarbons may be removed from the hydrocarbon mixture which is the product of the dehydrogenation of saturated linear hydrocarbons containing from about 7 to about 17 carbon atoms. It is also desirable to remove the aromatic hydrocarbons from the hydrocarbon product of the selective hydrogenation of alkadienes containing from about 10 to about 15 carbon atoms to their corresponding alkenes.

An additional specific embodiment of the invention is the separation of a solution of saturated hydrocarbons and unsaturated aliphatic hydrocarbons into a saturated hydrocarbon portion and an unsaturated hydrocarbon portion. The aliphatic hydrocarbons and desorbents discussed above also apply in this embodiment. Similarly, as discussed in the previous specific embodiment, the countercurrent simulated moving bed flow system providing a raffinate stream and an extract stream is preferred for these embodiments as well. In this embodiment, saturated hydrocarbons, as discussed above, as well as unsaturated aliphatic hydrocarbons and mixtures thereof, may be used as the desorbent. Suitable unsaturated aliphatic hydrocarbon desorbents generally contain from about 4 to about 18 carbon atoms. For environmental reasons, when operating in the liquid phase saturated hydrocarbon desorbents are the most preferred. A specific application of this embodiment is the separation of unsaturated aliphatic hydrocarbons from a mixture of unsaturated aliphatic hydrocarbons and saturated hydrocarbons containing from 4 to 18 carbon atoms.

Another specific embodiment of the invention is the separation of a solution of unsaturated aliphatic hydrocarbons into an alkene portion and an alkadiene portion. Typical suitable alkenes and alkadienes contain from about 4 to about 18 carbon atoms. Process conditions are optimized specifically to separate alkenes and alkadienes and the separation is accomplished where no aromatic or saturated hydrocarbons are present. As discussed in previous embodiments, the countercurrent simulated moving bed flow system providing a raffinate stream and an extract stream is preferred. The alkenes are less strongly adsorbed on the adsorbent than the alkadienes and consequently will be desorbed first and collected in the raffinate stream. The alkadienes are more strongly adsorbed on the adsorbent and will be carried with the adsorbent before being desorbed and collected in the extract stream.

The examples below are not intended as a limitation on the scope of the present invention and are merely illustrative of adsorbent performance. The examples employed the commonly used pulse test to evaluate various adsorbents with particular hydrocarbon solutions and desorbents to measure adsorption characteristics. The apparatus for this test consisted of an adsorbent chamber of approximately 5 cc volume having inlet and outlet portions at opposite ends of the chamber. The chamber was contained within a temperature control means and pressure control equipment was used to operate the chamber at a constant predetermined pressure. Analytical instrumentation was attached to the outlet line of the chamber to measure one or more components eluting from the chamber. To perform the test, the adsorbent was placed in the chamber and filled to equilibrium with the desorbent by passing the desorbent through the adsorbent chamber at approximately one linear space velocity. At a convenient time, a 5 $\mu$L pulse of the solution to be separated was injected, and then the desorbent flow was resumed. The components were eluted as in a liquid-solid chromatographic operation and could be analyzed on-line, or samples could be periodically collected and analyzed separately. Adsorbent performance may be rated from the results of this test. The pulse test described above, and used in the examples, is a reduced scale of the commonly used pulse test described in U.S. Pat. Nos. 5,220,102 and 3,855,333.

EXAMPLE 1

SEPARATION USING SILICA GEL

A pulse test, as described above, was performed using an adsorbent chamber, having inlet and outlet portions at opposite ends, which contained 5 cc of silica gel obtained from the Aldrich Company. The chamber was contained within a temperature control means to keep the temperature of the chamber at 60° C., and pressure control equipment was used to operate the chamber at a constant pressure of 500 psi. An on-line gas chromatograph was used to determine the components of the effluent stream leaving the adsorbent chamber. Desorbent, n-heptane, was passed through the adsorbent material at a flow rate of approximately one linear space velocity. At a particular time after equilibrium had been established, a 5 $\mu$L pulse of the solution to be separated, a mixture of n-nonane and aromatic hydrocarbons containing 8 carbon atoms, specifically, para-xylene, meta-xylene, ortho-xylene, and ethylbenzene, was injected. Desorbent flow was resumed and the effluent was analyzed periodically by the on-line gas chromatograph. As FIG. 1 illustrates, the n-nonane eluted, but the aromatic portion was so strongly retained on the silica gel that it did not desorb.

EXAMPLE 2

SEPARATION USING ALKYLENE-BRIDGED POLYSILSESQUIOXANE

Figure 2:
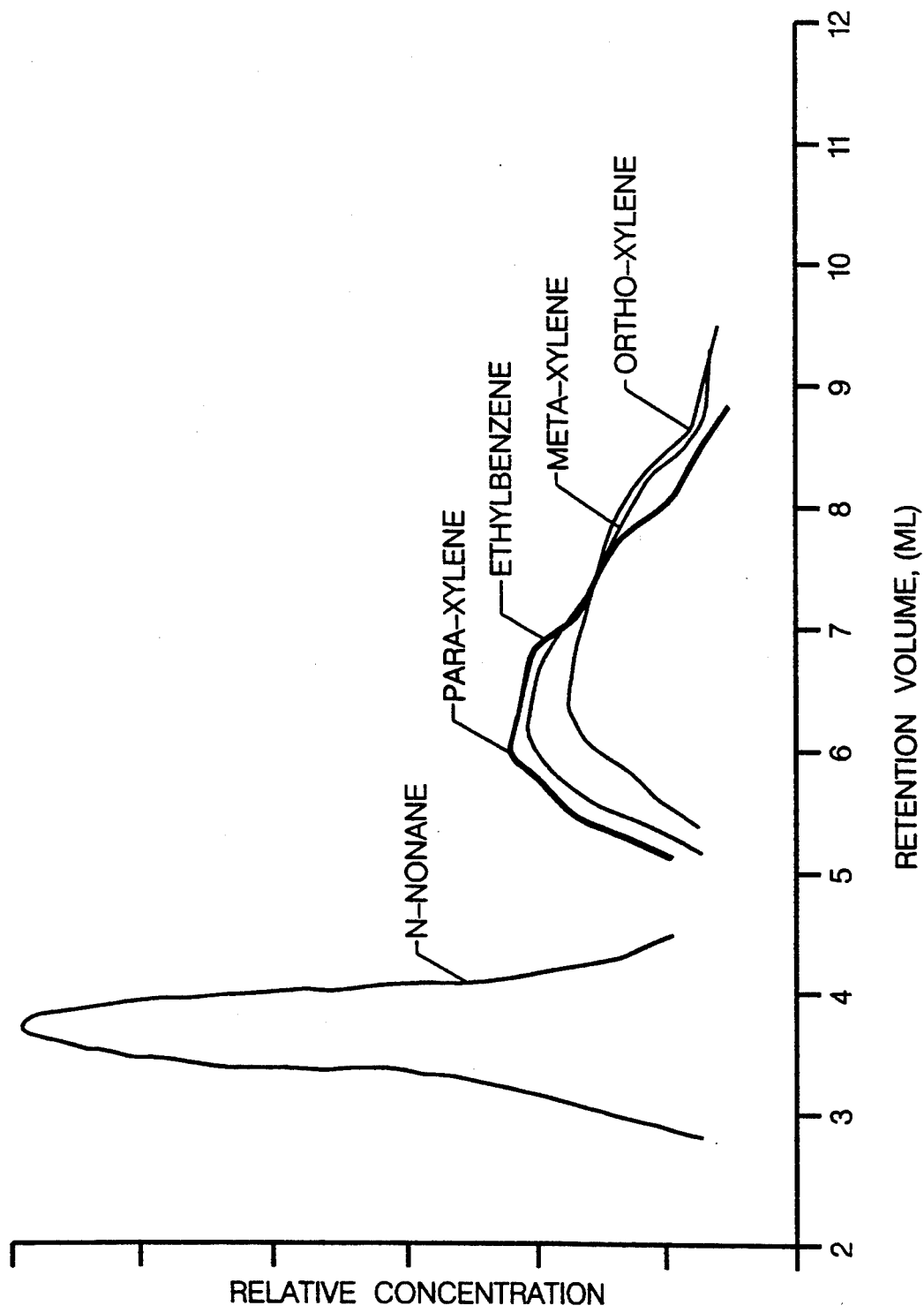
FIG. 2 is the chromatographic plot of the separation of a mixture of a saturated hydrocarbon and aromatic hydrocarbons using an alkylene-bridged polysilsesquioxane as the adsorbent as conducted in Example 2.

A pulse test, as described above, was performed using an adsorbent chamber, having inlet and outlet portions at opposite ends, which contained 5 cc of ethylene-bridged polysilsesquioxane gel. The chamber was contained within a temperature control means to keep the chamber at 60° C. and pressure control equipment was used to operate the chamber at a constant pressure of 500 psi. An on-line gas chromatograph was used to determine the components of the effluent stream leaving the adsorbent chamber. Desorbent, n-heptane, was passed through the adsorbent material at a flow rate of approximately one linear space velocity. At a particular time after equilibrium had been established, a 5 $\mu$L pulse of the solution to be separated, a mixture of n-nonane, ethylbenzene, para-xylene, meta-xylene, and ortho-xylene, was injected. Desorbent flow was resumed, and the effluent was analyzed periodically by the on-line gas chromatograph. As FIG. 2 illustrates, the n-nonane eluted first and had completely eluted before the aromatic compounds began to elute. The aromatic compounds eluted simultaneously as a class of hydrocarbons. The saturated hydrocarbon was easily separated from the aromatic hydrocarbons.

EXAMPLE 3

SEPARATION USING ALKYLENE-BRIDGED POLYSILSESQUIOXANE

Figure 3:
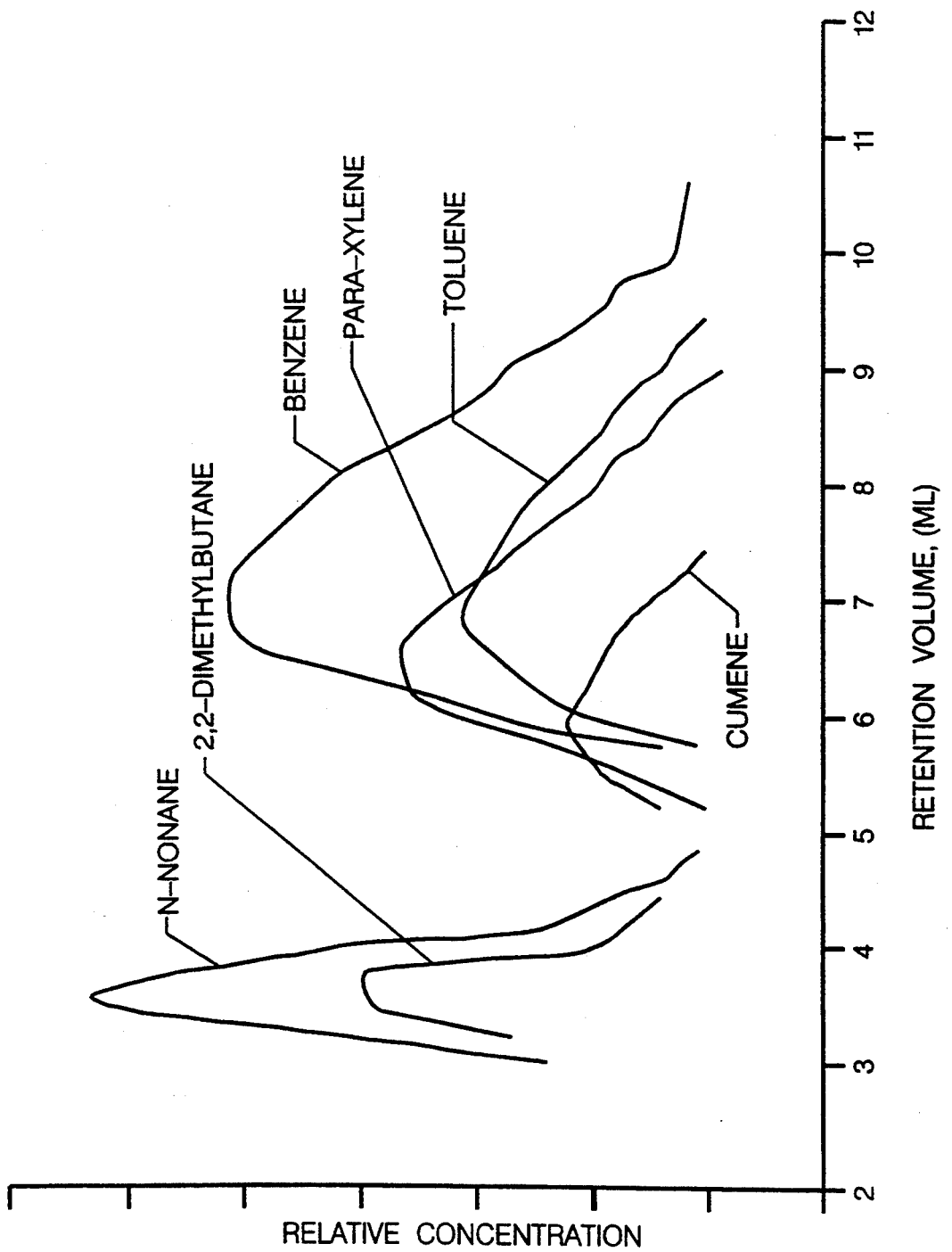
FIG. 3 is the chromatographic plot of the separation of a mixture of saturated hydrocarbons and aromatic hydrocarbons using an alkylene-bridged polysilsesquioxane as the adsorbent as conducted in Example 3.

A pulse test, as described above, was performed using an adsorbent chamber, having inlet and outlet portions at opposite ends, which contained 5 cc of ethylene-bridged polysilsesquioxane gel. The chamber was contained within a temperature control means to keep the chamber at 60° C. and pressure control equipment was used to operate the chamber at a constant pressure of 500 psi. An on-line gas chromatograph was used to determine the components of the effluent stream leaving the adsorbent chamber. Desorbent, n-heptane, was passed through the adsorbent material at a flow rate of approximately one linear space velocity. At a particular time after equilibrium had been established, a 5 μL pulse of the solution to be separated, a mixture of n-nonane, 2,2-dimethylbutane, ethylbenzene, para-xylene, meta-xylene, ortho-xylene, and cumene was injected. Desorbent flow was resumed, and the effluent was analyzed periodically by the on-line gas chromatograph. As FIG. 3 illustrates, the n-nonane and the 2,2-dimethylbutane simultaneously eluted as a class of hydrocarbons and had completely eluted before the aromatic compounds began to elute. The aromatic compounds then eluted simultaneously as a class of hydrocarbons. The saturated hydrocarbons were easily separated from the aromatic hydrocarbons.

EXAMPLE 4

SEPARATION USING ALKYLENE-BRIDGED POLYSILSESQUIOXANE

Figure 4:
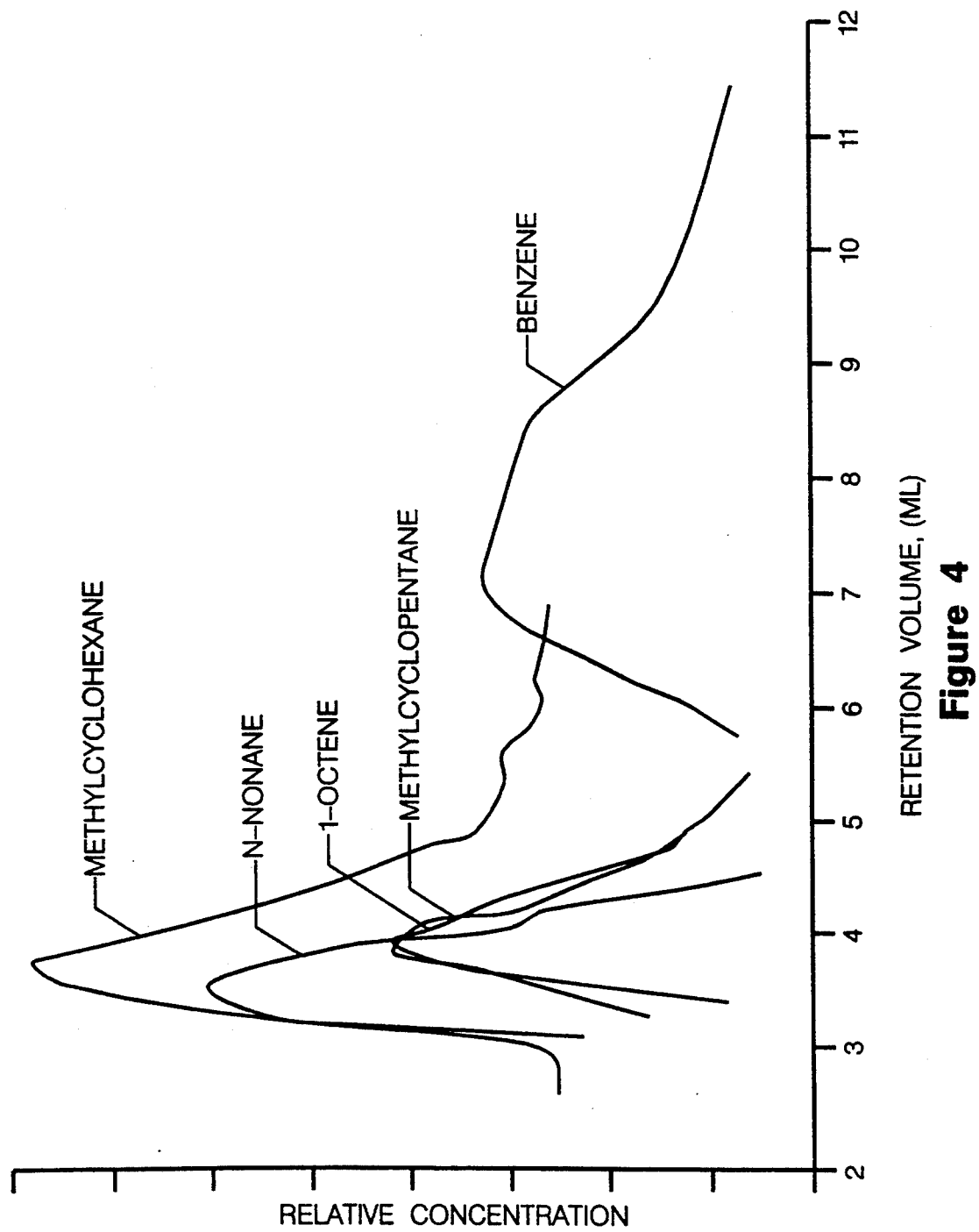
FIG. 4 is the chromatographic plot of the separation of a mixture of saturated hydrocarbons, an unsaturated aliphatic hydrocarbon, and aromatic hydrocarbons using an alkylene-bridged polysilsesquioxane as the adsorbent as conducted in Example 4.

A pulse test, as described above, was performed using an adsorbent chamber, having inlet and outlet portions at opposite ends, which contained 5 cc of ethylene-bridged polysilsesquioxane gel. The chamber was contained within a temperature control means to keep the chamber at 60° C. and pressure control equipment was used to operate the chamber at a constant pressure of 500 psi. An on-line gas chromatograph was used to determine the components of the effluent stream leaving the adsorbent chamber. Desorbent, n-heptane, was passed through the adsorbent material at a flow rate of approximately one linear space velocity. At a particular time after equilibrium had been established, a 5 μL pulse of the solution to be separated, a mixture of n-nonane, methylcyclopentane, methylcyclohexane, 1-octene, and benzene was injected. Desorbent flow was resumed, and the effluent was analyzed periodically by the on-line gas chromatograph. As FIG. 4 illustrates, the aromatic compound, benzene, eluted last and is easily separated from the rest of the components. The n-nonane, methylcyclohexane, and methylcyclopentane, eluted first at approximately the same time with the 1-octene eluting shortly thereafter. FIG. 4 clearly demonstrates the separation of a solution of aromatic hydrocarbons and aliphatic hydrocarbons into an aromatic hydrocarbon portion and an aliphatic hydrocarbon portion, the aliphatic portion being a combination of saturated hydrocarbons and unsaturated aliphatic hydrocarbons, and with optimization of the conditions, applicants believe the separation of the saturated and unsaturated aliphatic components would become more significant thus enabling the mixture to be separated into a saturated hydrocarbon portion, an unsaturated aliphatic hydrocarbon portion and an aromatic portion.

What is claimed is:

1. A process for separating, into hydrocarbon classes, the components of a solution containing at least two classes of hydrocarbons selected from the group consisting of saturated hydrocarbons, unsaturated aliphatic hydrocarbons, and aromatic hydrocarbons, comprising:
   a. contacting said solution with an alkylene-bridged polysilsesquioxane adsorbent where said alkylene-bridging group contains from about 2 to about 14 carbon atoms, said adsorbent effective to adsorb hydrocarbons with increasing strength in the order of saturated hydrocarbons < unsaturated aliphatic hydrocarbons < aromatic hydrocarbons;
   b. desorbing the adsorbed saturated hydrocarbons, where present, from said adsorbent using a desorbent, and collecting the desorbed saturated hydrocarbons;
   c. desorbing the adsorbed unsaturated aliphatic hydrocarbons, where present, from said adsorbent using said desorbent, and collecting the desorbed unsaturated aliphatic hydrocarbons; and
   d. desorbing the adsorbed aromatic hydrocarbons, where present, from said adsorbent using said desorbent, and collecting the desorbed aromatic hydrocarbons.

2. The process of claim 1 where the alkylene-bridging group is ethylene.

3. The process of claim 1 where the process is operated in a simulated moving bed mode.

4. The process of claim 1 where the process is operated in a fixed bed mode.

5. The process of claim 1 where the classes of hydrocarbons in the solution are saturated hydrocarbons, unsaturated aliphatic hydrocarbons, and aromatic hydrocarbons.

6. The process of claim 1 where the classes of hydrocarbons in the solution are saturated hydrocarbons and unsaturated aliphatic hydrocarbons.

7. The process of claim 1 further characterized in that aromatic hydrocarbons are separated as one class of hydrocarbons and saturated hydrocarbons and unsaturated aliphatic hydrocarbons are separated as a second class of hydrocarbons.

8. The process of claim 1 where said process is operated in the liquid phase.

9. The process of claim 8 where said desorbent is a saturated hydrocarbon, an unsaturated aliphatic hydrocarbon, or a combination thereof.

10. The process of claim 8 where said desorbent is a saturated hydrocarbon.

11. The process of claim 8 where the classes of hydrocarbons in the solution are saturated hydrocarbons and unsaturated aliphatic hydrocarbons, and where said desorbent is an unsaturated aliphatic hydrocarbon.

12. The process of claim 8 where the classes of hydrocarbons in the solution are saturated hydrocarbons and unsaturated aliphatic hydrocarbons, and where said desorbent is a mixture of an unsaturated aliphatic hydrocarbon and a saturated hydrocarbon.

13. The process of claim 1 where said process is operated in the gas phase.

14. The process of claim 13 where the desorbent is selected from the group consisting of hydrogen, nitrogen and helium.

15. A process for separating, into hydrocarbon classes, the components of an unsaturated aliphatic hydrocarbon solution containing alkenes and alkadienes, comprising:
   a. contacting said solution with an alkylene-bridged polysilsesquioxane adsorbent where said alkylene-bridging group contains from about 2 to about 14 carbon atoms, said adsorbent effective to adsorb hydrocarbons with increasing strength in the order of alkenes<alkadienes;
   b. desorbing the adsorbed alkenes from said adsorbent using a desorbent, and collecting the desorbed alkenes; and
   c. desorbing the adsorbed alkadienes from said adsorbent using said desorbent and collecting the desorbed alkadienes.

16. The process of claim 15 where the alkylene-bridging group is ethylene.

17. The process of claim 15 where the process is operated in a simulated moving bed mode.

18. The process of claim 1 where the process is operated in a fixed bed mode.

19. The process of claim 15 where said process is operated in the liquid phase.

20. The process of claim 19 where said desorbent is a saturated hydrocarbon, an unsaturated aliphatic hydrocarbon, or a combination thereof.

21. The process of claim 19 where said desorbent is a saturated hydrocarbon.

22. The process of claim 15 where said process is operated in the gas phase.

23. The process of claim 22 where the desorbent is selected from the group consisting of hydrogen, nitrogen and helium.

* * * * *

UNITED STATES PATENT AND TRADEMARK OFFICE
CERTIFICATE OF CORRECTION

PATENT NO. : 5,449,853
DATED : September 12, 1995
INVENTOR(S) : James R. Lansbarkis, et. al.

It is certified that error appears in the above-indentified patent and that said Letters Patent is hereby corrected as shown below:

In column 1, line 65, the symbol "░" should be inserted between the words "the" and "represents"; in column 2 line 10 centered below the structure insert --I--. In column 2 line 16, centered below the structure insert --II--; in column 2, lines 1-9, the structure should read as follows:

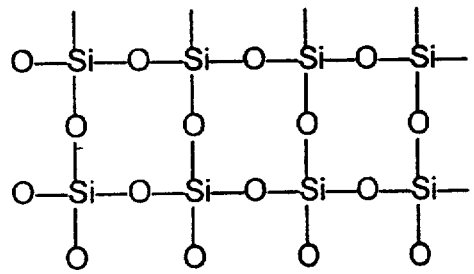

I

UNITED STATES PATENT AND TRADEMARK OFFICE
CERTIFICATE OF CORRECTION

PATENT NO. : 5,449,853
DATED : September 12, 1995
INVENTOR(S) : James R. Lansbarkis, et. al.

It is certified that error appears in the above-indentified patent and that said Letters Patent is hereby corrected as shown below:

In column 2, lines 10-15, the structure should read as follows:

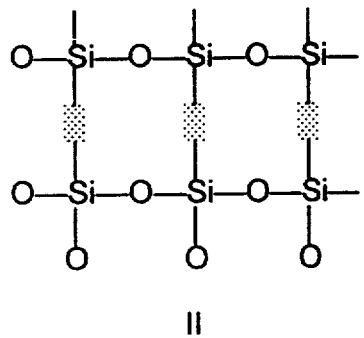

Signed and Sealed this

Thirtieth Day of January, 1996

Attest:

BRUCE LEHMAN

Attesting Officer

Commissioner of Patents and Trademarks